(12) United States Patent
Bracht

(10) Patent No.: US 10,653,636 B2
(45) Date of Patent: May 19, 2020

(54) MEDICAL ACTIVE SUBSTANCE PATCH WITH REDUCED OPTICAL CONSPICUOUSNESS ON THE SKIN

(75) Inventor: Stefan Bracht, Cospeda (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 2028 days.

(21) Appl. No.: 10/553,708

(22) PCT Filed: Apr. 8, 2004

(86) PCT No.: PCT/EP2004/003748
§ 371 (c)(1),
(2), (4) Date: Jun. 16, 2006

(87) PCT Pub. No.: WO2004/091590
PCT Pub. Date: Oct. 28, 2004

(65) Prior Publication Data
US 2007/0116751 A1 May 24, 2007

(30) Foreign Application Priority Data
Apr. 17, 2003 (DE) .................................. 103 17 692

(51) Int. Cl.
*A61K 9/70* (2006.01)
(52) U.S. Cl.
CPC ............ *A61K 9/703* (2013.01); *A61K 9/7023* (2013.01)
(58) Field of Classification Search
None
See application file for complete search history.

(56) References Cited

U.S. PATENT DOCUMENTS

| | | | |
|---|---|---|---|
| 5,004,610 A * | 4/1991 | Osborne et al. | 424/448 |
| 5,120,325 A * | 6/1992 | Dow, Jr. | 604/304 |
| 5,372,819 A * | 12/1994 | Godbey et al. | 424/449 |
| 5,676,969 A * | 10/1997 | Wick | A61K 9/7084 424/447 |
| 6,080,421 A | 6/2000 | Steinborn et al. | |
| 6,361,790 B1 * | 3/2002 | Rolf et al. | 424/443 |
| 7,622,136 B2 * | 11/2009 | Gale | 424/449 |

FOREIGN PATENT DOCUMENTS

| | | |
|---|---|---|
| CA | 2366859 | 9/2000 |
| DE | 7529365 | 1/1976 |
| DE | 4030465 | 4/1992 |
| DE | 19519593 | 8/1996 |
| DE | 19912623 | 9/2000 |
| DE | 10053375 C1 * | 1/2002 |
| JP | 62-195073 | 8/1987 |
| JP | 7-206624 | 8/1995 |
| WO | WO 00/37058 | 6/2000 |
| WO | WO 01/78678 | 10/2001 |
| WO | WO 0178678 A1 * | 10/2001 |
| WO | WO 02/34200 | 5/2002 |
| WO | WO 0234200 A2 * | 5/2002 |

OTHER PUBLICATIONS

"4-aminobenzoic acid", encyclopedia.*
"Cinnamic Acid", product identification.*
"Benzophenone", IngredientsFeedbackScience.*
"Lacquer definition", Your Dictionary.*
"Merriam Webster Dictionary", difinition of "pigment".*
"Doctor's Guide to Medical & Other News" (Excerpt); www.pslgroup.com (Apr. 18, 2000).
Test results of lightness values NICODERM® CQ® Patch (Apr. 24, 2008).
Screen shot advertisement "Clear NICODERM® CQ®" (May 8, 2008).
Notice of Opposition to European Patent No. 1615628 (Sep. 3, 2009).
Report of Test Results; Japan Paint Inspection and Testing Association (Apr. 24, 2008).
Product Information; NicoDerm CQ (May 8, 2008).
www.docguide.com; Clear NicoDerm CQ; *Medical & Other News* (Apr. 18, 2000).

* cited by examiner

*Primary Examiner* — Kevin S Orwig
(74) *Attorney, Agent, or Firm* — ProPat, LLC; Cathy R. Moore

(57) ABSTRACT

A medical active substance patch comprising a matrix of monolayer or multilayer configuration with at least one active substance-containing layer and comprising a backing layer connected with the matrix. The active substance patch is transparent or at least translucent, and in the state of having been applied to the skin of a first person, the patch has a lightness colour value $L_1$ at a place of the skin covered by the patch which is not less than 50% and not more than 200% of a lightness colour value $L_2$, $L_2$ being the lightness value of the region of the skin of the same person which surrounds the applied patch. The same is true of the skin of a second or any other person, provided that for all the persons mentioned $L_2$ is in the range from 5° to 100°, namely from 20° to 90°.

17 Claims, 1 Drawing Sheet

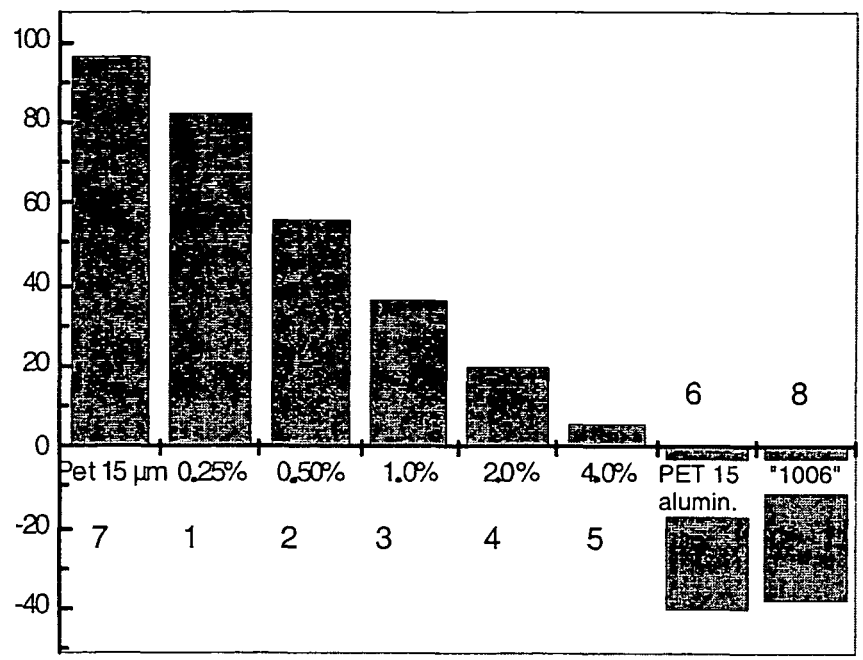

MEDICAL ACTIVE SUBSTANCE PATCH WITH REDUCED OPTICAL CONSPICUOUSNESS ON THE SKIN

CROSS-REFERENCE TO RELATED APPLICATIONS

This application is a National Stage application of International Application No. PCT/EP2004/003748, filed on Apr. 8, 2004, which claims priority of German application number 103 17 692.6, filed on Apr. 17, 2003.

BACKGROUND OF THE INVENTION

Field of the Invention

The present invention relates to medical active substance patches, particularly to transdermal therapeutic systems, comprising a monolayer or multilayer, active substance-containing matrix and a backing layer connected with the matrix, the active substance patches being distinguished by an improved optical appearance when being worn on the skin.

The invention further encompasses processes enabling the production of such active substance patches.

Description of the Prior Art

Many of the active substances or auxiliary agents suitable for use in the manufacture of active substance patches or TTSs show a tendency to discolour, for example to yellow. Such adverse changes may also occur during the application period. It is known, for instance, that nicotine patches gradually turn yellow.

The aforementioned changes are in most cases due to oxidative decomposition processes which progress upon contact with atmospheric oxygen and moisture especially during storage of the active substance patch or when it is being worn on the skin and which are promoted by action of light. Particularly affected by such processes are pharmaceutical active substances, antioxidants, various enhancers (i.e. substances promoting or accelerating transdermal active substance absorption), as well as oxidation-sensitive components of the pressure-sensitive adhesive that is present in the active substance patch, such as resin adhesives, for example.

The extent of active substance decomposition does not necessarily have an adverse effect on the pharmaceutical quality of the products, for instance if the resulting decomposition products amount to only fractions of a weight percent of the starting composition and if these decomposition products are toxicologically acceptable. Thus, discolouration often already affects a product cosmetically whereas the pharmaceutical quality is still unimpaired. Frequently, users or patients especially in the case of medicaments associate such disadvantageous changes in the optical appearance of the active substance patches with defectiveness or deterioration, which causes a feeling of insecurity in those patients.

Often these changes are yellow, brown or red discolourations as typically appear in chemical decomposition. Even slight changes in colour may be interpreted by the users or patients as indicative of a deterioration of the quality of the medicament.

The problem of discolouration occurs particularly if the product, in fresh condition after manufacture, initially appears colourless or white to the human eye and the above-mentioned discolouration occurs only after a certain period of storage or while the patch is being worn on the skin. This is perceived by the users to be even more critical and potentially dangerous than a discolouration which has been there from the start and only becomes more intense during storage.

In the field of medical active substance patches, transparent and colourless patches represent the ideal case in respect of cosmetics since the user himself or other persons regard them as inconspicuous when applied to the user's skin. Users of medicinal patches generally prefer patches with such inconspicuous properties because they reduce the risk of other people becoming aware of the user's need for treatment and possibly finding out about his illness.

If for reasons of cosmetics a transparent design of an active substance patch does not make sense, for example because the ingredients are coloured or because of discolouration occurring during storage, it is possible to equip the patch with a non-transparent backing layer. During the application period, this backing layer then prevents the colour or discolouration from being optically perceived.

In the latter case, it is disadvantageous, however, that patches or TTSs equipped with a nontransparent backing layer are much more conspicuous at the site of application, that is, on the patient's skin, than transparent or colourless patches. A measure known from the state of the art and frequently applied consists in applying a skin-coloured lacquer to the nontransparent backing layer. This, however, leads to a further problem since it proves extremely difficult to find a skin tone that in equal measure suits a larger number of users of different skin colour tone and is cosmetically acceptable. Taking into consideration all of the skin types of the world population, it is entirely impossible to determine a unitary, opaque skin colour tone that would be suitable as the colour tone for a non-transparent backing layer. This problem could be solved, it is true, by producing otherwise identical active substance patches having differently coloured backing layers that match the different skin colour tones of the world population, but this is out of the question because of the complex manufacturing and distribution logistics, and ultimately for reasons of cost.

SUMMARY OF THE INVENTION

The object of the present invention was therefore to provide active substance patches which despite colourations that are already existent or occurring over time ensure an optically inconspicuous appearance of the patch especially when the patch is located at the application site. The intention here is to preferably find a uniform solution which is suitable for the most different skin colour tones of the world population.

A further object of the invention was to indicate processes by which such active substance patches can be obtained.

These objects are achieved by medical active substance patches according to the present invention and by processes of production according to the present invention.

Thus, the above-mentioned disadvantages do not occur or only occur in attenuated form in the medical active substance patches according to the present invention if the active substance patch is transparent or at least translucent and if—in the state of having been applied to a person's skin—the patch, in an area of the skin covered with the patch, has a lightness colour value $L_1$ which is not less than 50% and not more than 200% of a lightness colour value $L_2$, $L_2$ being the lightness value of the region of the skin of the same person which surrounds the applied patch, and if the same is true in respect of the skin of a second or any other person, provided that $L_2$, for all the persons mentioned, is in a range from 5° to 100°, especially in a range from 20° to 90°. The aforementioned differences between the lightness values $L_1$, $L_2$ can be determined by measurements in representative spot checks of people of the respective skin type.

The colour value of the lightness L, designated as "lightness colour value" is a calorimetric characteristic value which, in conjunction with other characteristics, is used in engineering for the non-ambiguous characterisation of colours. The lightness colour value is indicated in degrees and can be determined by colour measuring instruments. The values of colour lightness indicated herein were determined by a "tristimulus colorimeter CP-320" of the firm of Techkon GmbH (DE-61462 Königstein).

Surprisingly, it emerged that active substance patches having the aforementioned features of the invention were of inconspicuous appearance at the place of application, i.e. on the skin, and that such active substance patches are optically inconspicuous on the most different skin colour types of the world population. For example, an active substance patch of the invention has an equally inconspicuous optical appearance when applied to the skin of a user of Caucasian, light skin colour or to the skin of a user of dark, Negroid skin colour. For this reason, according to one embodiment an active substance patch of the invention comprises the lightness colour value $L_2$ of the first person, measured in the area of the skin not covered by the patch, is the lightness colour value of a person of light, Caucasian skin colour, and that the lightness colour value $L_2$ of the second person is the lightness colour value of a person of dark, negroid skin colour, or vice versa.

The manufacture of active substance patches having the features of the present invention and the substances suitable for the manufacture are in principle known to those skilled in the art. Substances which may be used to produce the matrix layer(s) are, for instance, from the group of the polyacrylates, poly(meth)acrylates, adhesive resins, cellulose derivatives, polyisobutylenes, styrene-isoprene-styrene block copolymers, styrene-butadiene-styrene block copolymers, polydimethyl siloxane, ethylene vinyl acetate copolymers and vinyl acetate, optionally with addition of auxiliary substances known to the skilled artisan. At least one of the matrix layers contains an active substance, the term active substance referring, in particular, to a pharmaceutical active substance or a plurality of such substances.

The active substance patches of the invention, which are composed of a matrix and a superimposed backing layer, are substantially transparent or at least translucent (i.e. transmitting light but not transparent) and in any case not opaque. Thus, the backing layer is also substantially transparent or translucent.

Suitable as a backing layer are, first of all, polyesters, such as polyethylene terephthalate (PET) and polybutylene terephthalate, but also almost any other skin-compatible plastics, such as polyvinyl chloride, ethylene vinyl acetate, vinyl acetate, polyethylene, polypropylene, cellulose derivatives and many others.

According to one embodiment, the active substance patches of the invention contain one or more substances from the group of the dyes and pigments in at least one of their layers. In combination with the transparent or translucent properties of the patch it is thereby achieved that a colouration of the matrix ingredient(s) which has been existing from the start or a discolouration of the ingredients which has begun and intensifies only after the patch has been manufactured is optically masked. At the same time, the colour is thereby sufficiently adapted to the skin tone of the application site so that the patch will be inconspicuous on the most different skin colour types. The substance(s) used for optical masking, which are selected from the group of the dyes and pigments, are contained in the matrix layer or in at least one of the matrix layers of a multilayer patch.

According to a further embodiment, optical masking is achieved by providing the transparent or translucent backing layer with a content of at least one substance selected from the group of the dyes and pigments. This can be accomplished, in particular, by coating the backing layer of the patch on its outer side, that is, on the side averted from the skin, with a coating or a lacquer which contains at least one dye or/and at least one pigment. This variant has the additional advantage that the dye(s) or pigment(s) cannot come into contact with the active substance-containing matrix.

It may further be advantageous for both the matrix layer(s) and the backing layer to contain, i.e., the backing layer is coated on its outer side, (e.g., is associated with) with a dye or dyes and/or a pigment or pigments.

It has, surprisingly, emerged that it is not so much the adaptation of the dyes or pigments to the respective skin tone which is decisive, rather this effect is essentially determined by the concentration(s) of the dyes or/and pigments utilised. The optical conspicuousness of an active substance patch is substantially determined by the concentrations of the dyes and pigments contained therein. In addition, the layer thickness of the patch must be taken into consideration in this connection. In order for the patch to be inconspicuous to the eye of a beholder, certain concentrations of the dyes or/and pigments (inclusive of the coloured or discoloured ingredients, in particular active substances) must not be exceeded. These concentrations can be determined by the disclosed conditions.

At low concentrations of the coloured or discoloured ingredients comprised in the matrix, even such dyes or pigments can still be optically inconspicuous as clearly deviate from the colour tone of the underlying skin at the place of application. The same applies if the patch is of a small layer thickness. The low concentration and/or the small layer thickness results in a scope for the concentration or in corresponding possibilities of varying the layer thickness, thus fulfilling the requirements for optical masking of discolourations of ingredients of active substance patches by admixing dyes or/and pigments.

A further improvement of the optical appearance of active substance patches applied to the skin can be achieved, according to an additional embodiment, by providing at least the surface of the backing layer which is averted from the skin with reduced reflection properties. This can either be accomplished by physical methods or by applying an antireflection layer or antireflection coating. Such a layer or coating contains an optical dulling agent or a combination of at least two dulling agents. This antireflection layer may at the same time contain a dye or dyes or/and a pigment or pigments to mask the ingredients of the patch, as described above.

In addition, it is possible by matting to eliminate or reduce the cause of optical conspicuousness of an active substance patch which is due to light reflection. Such light reflection frequently occurs in active substance patches which are provided with a transparent backing layer of smooth surface structure. The reflection properties of these backing layer materials differ greatly from the reflection properties of human skin, which is why such plasters are visually very conspicuous on the skin.

The active substance patches of the present invention are particularly advantageous if at least one layer of the matrix comprises one or more coloured ingredient(s). This may, in particular, be a substance or substances which is/are colourless in its/their initial state and which has/have a tendency to discolour or which discolour during storage or during the application period. Particularly preferred are active substance patches which contain one or more pharmaceutically active substances as coloured ingredients or as ingredients which have a tendency to discolour, such as for nicotine.

The active substance patches mentioned may be transdermal therapeutic systems. These are distinguished by enabling a constant delivery of active substances via the skin for a determined period of time. The structure and manufacture of such systems are in principle known to those skilled in the art.

The present invention further encompasses processes for the production of the above-described active substance patches. These processes comprise the following steps:

(a) producing a system comprising a mono- or multilayer active substance-containing matrix and a backing layer connected therewith, wherein the matrix is produced by using (a) matrix polymer(s), (an) active substance(s) and auxiliary agents, and wherein one or more substance(s) selected from the group of the dyes and pigments is/are admixed to the matrix or/and the backing layer;

(b) producing at least one further system according to step (a), this system being different in terms of the concentration of the dyes or/and pigments, and/or in terms of the type of the dyes or/and pigments used;

(c) producing surface sections or punched pieces from the systems obtained in steps (a) and (b);

(d) producing or providing colour charts with lightness colour values $L_2$ in the range from 5° to 100°, particularly in the range from 20° to 90°, (e) applying or affixing the sections or systems obtained in step (c) to the colour charts mentioned in (d);

(f) measuring the colour values of the lightness $L_1$ of the systems located on the colour charts and determining the difference between $L_2$ and $L_1$ in each particular case;

(g) selecting those systems with a colour value of the lightness $L_1$ which is not less than 50% and not more than 200% of the lightness colour value $L_2$.

Through the teaching of the present invention it is made possible to produce active substance patches which despite containing coloured or discolouring ingredients are not easily perceivable to an observer and are optically inconspicuous when being worn on the skin, independently of whether the patch is attached to the skin of a light-skinned or dark-skinned person.

BRIEF DESCRIPTION OF THE DRAWINGS

FIG. 1 is a bar graph depicting individual test patches Nos. 1-8 in the order of their visual inconspicuousness.

DETAILED DESCRIPTION OF THE INVENTION

The invention will be illustrated in greater detail by the following examples.

EXAMPLES

1. Preparation of Backing Layers of Different Pigment Concentrations

Coating compounds were prepared from ethyl cellulose and different portions of a pigment mixture (see Table 1) and these compounds were coated by a doctor knife to a PET film of 15 μm thickness (weight per unit area 7-10 g/m$^2$).

TABLE 1

| No. | Ethyl cellulose [%-wt.] | Pigment mixture [%-wt.] |
|---|---|---|
| 1 | 99.75 | 0.25 |
| 2 | 99.5 | 0.5 |
| 3 | 99.0 | 1.0 |
| 4 | 98.0 | 2.0 |
| 5 | 96.0 | 4.0 |

Pigment Mixture:

50.0%-wt. of Naturell BB Plv™ Pigment 50.0%-wt. of Naturell Pulver™ Pigment (from Cosnaderm Chemische Rohstoffe GmbH, D-68526 Ladenburg)

Used as control examples were:

(6) PET film, aluminised and nicotine-resistant (nontranslucent)

(7) PET film, 15 μm, transparent (8) SCOTCHPAK® (a plastic film) 1006

2. Preparation of Skin Patches

Skin patches were produced using the backing layers prepared under 1. To this end, DUROTAK® 2052 (National Starch & Chemical B.V.) (a pressure sensitive adhesive) was spread at a weight per unit area of 80 g/m$^2$ and in each case covered with one of the backing layers mentioned under 1. Subsequently, individual patches, each patch of a size of 1 cm$^2$, were punched out.

3. Preparing Colour Charts Corresponding to the Human Skin Colours

By use of the software "PowerPoint" (Microsoft) and a colour printer (HP-C LaserJet 4500; Hewlett-Packard) eight colour charts were established representing the various skin colour tones of the world population.

The colour tones of the colour charts are set forth in "PowerPoint" by the six parameters colour tone, red, green, blue, saturation, intensity as listed below, and can be reproduced by these parameters:

TABLE 2

| Colour chart No. | Colour tone | Red | Green | Blue | Saturation | Intensity |
|---|---|---|---|---|---|---|
| A | 16 | 255 | 215 | 191 | 255 | 223 |
| B | 21 | 50 | 25 | 0 | 255 | 25 |
| C | 21 | 80 | 40 | 0 | 255 | 40 |
| D | 21 | 255 | 236 | 217 | 255 | 236 |
| E | 21 | 197 | 137 | 77 | 130 | 137 |
| F | 21 | 72 | 36 | 0 | 255 | 36 |
| G | 21 | 117 | 78 | 39 | 128 | 78 |
| H | 25 | 255 | 226 | 183 | 255 | 219 |

The colour charts Nos. A-H were measured using a "tristimulus colorimeter CP-320" of the firm of Techkon GmbH (DE-61462 Königstein). The values (in degrees) for the lightness L, the red-green axis a, and the yellow-blue axis b were determined. For each colour chart, 10 measurements were made and the mean values determined. The mean values are represented in the following Table 3.

TABLE 3

| Colour chart No. | L Value ($L_2$) | a Value | b Value |
|---|---|---|---|
| A | 82.464 | 10.986 | 13.634 |
| B | 21.791 | −3.203 | 8.877 |
| C | 25.776 | 5.905 | 14.758 |
| D | 88.086 | 4.945 | 9.572 |
| E | 50.596 | 10.893 | 36.304 |
| F | 25.811 | 3.747 | 12.968 |
| G | 32.562 | 5.519 | 21.015 |
| H | 83.228 | 6.712 | 24.95 |
| Mean value* | 51.289 | 5.688 | 17.758 |

*These are the respective mean values determined using the values of the 8 colour charts.

As can be seen, the colour value of the lightness L varies most, whereas the "a" value differs only slightly.

The range of the skin colours for which the principle of the present invention can be advantageously employed, according to the above-described "L, a, B" system particularly comprises the range of "5, 8, 60" up to "100, 4, 0".

4. Determining the Differences in Lightness Value

The punched skin patches described under 2 were adhered to the colour charts described under 3. Subsequently, the lightness colour values $L_1$ of the affixed patches were determined using the measuring method described under 3. From the measurement values $L_1$ obtained, the difference to the lightness value $L_2$ of the respective background (i.e. the colour chart) was determined in each case. The percentage differences between the lightness colour values $L_1$ of the patch types (Nos. 1 to 5 and controls Nos. 6 to 8) affixed to the colour charts A to H on the one hand and the lightness values $L_2$ of the respective colour charts A to H on the other hand are represented in Table 4.

It is evident therefrom that on all the colour charts the transparent PET film (7) shows the smallest deviations in respect of the lightness value (positive control).

Conversely, the largest deviations were found in the control examples (6) and (8).

5. Visual Evaluation

Since it is known that the colour perception of humans can deviate from the calorimetrically determined data, a visual assessment of the test patches affixed to the colour charts A to H, inclusive of the comparison examples 6 to 8, was carried out by test subjects.

To this end, a certain number (e.g. 10) of each of the test patches (1 to 8) was affixed to the colour charts A to H. These colour charts were presented to a group of test subjects under standardized conditions (lighting, distance, time for observing). The number of the patches that were not detected by the probands was used—after statistical evaluation of the data—as a measure for the optical inconspicuousness and thereby the effectiveness of the optical masking of a patch.

In FIG. 1 the individual test patches Nos. 1-8 are represented in the form of a bar chart in the order of their visual inconspicuousness (vertical axis). Patch No. 1 and control patch No. 7 were not perceivable or hardly perceivable on most of the colour charts.

TABLE 4

| | 15 μM trsp. (No. 7) | | nontransparent PET film 15 μm, alum. |
|---|---|---|---|
| | L | | L |
| A | 2.733 | A | 1.42 |
| B | 13.735 | B | 273 |
| C | 3.236 | C | 215 |
| D | 5.244 | D | 7.89 |
| E | 1.435 | E | 60.3 |
| F | 12.254 | F | 215 |
| G | 1.388 | G | 150 |
| H | 5.022 | H | 2.65 |

| Scotchpak 1006 (No. 8) | | 0.25% Pigment (No. 1) | |
|---|---|---|---|
| | L | | L |
| A | 2.903 | A | 6.5 |
| B | 267.078 | B | 25.5 |
| C | 210.289 | C | 12.6 |
| D | 9.157 | D | 8.13 |
| E | 58.254 | E | 6.35 |
| F | 209.79 | F | 17.8 |
| G | 144.61 | G | 7.07 |
| H | 4.059 | H | 7.51 |

| 0.50% Pigment (No. 2) | | 1.00% Pigment (No. 3) | |
|---|---|---|---|
| | L | | L |
| A | 6.978 | A | 9.94 |
| B | 22.133 | B | 7.81 |
| C | 7.294 | C | 1.51 |
| D | 5.325 | D | 10.6 |
| E | 4.577 | E | 6.4 |
| F | 17.144 | F | 10.8 |
| G | 4.53 | G | 3.19 |
| H | 3.189 | H | 10.2 |

| 2.00% Pigment (No. 4) | | 4.00% Pigment (No. 5) | |
|---|---|---|---|
| | L | | L |
| A | 14.387 | A | 9.29 |
| B | 1.647 | B | 54.5 |
| C | 4.058 | C | 19.2 |
| D | 8.295 | D | 21.6 |
| E | 33.528 | E | 4.53 |
| F | 1.794 | F | 28.4 |
| G | 2.709 | G | 17.9 |
| H | 13.731 | H | 20 |

What has been described above are preferred aspects of the present invention. It is of course not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, combinations, modifications, and variations that fall within the spirit and scope of the appended claims.

The invention claimed is:

1. A medical active substance patch that is optically inconspicuous when worn on the skin, independent of whether the patch is attached to a light-skinned person or a stark-skinned person, comprising a monolayer or multilayer matrix and a backing layer connected with said matrix, said backing layer having one side averted from the skin, wherein at least one layer of the matrix contains a pharmaceutically active substance, and wherein at least one layer of the matrix contains an ingredient selected from the group consisting of at least one coloured ingredient, and at least one colourless ingredient being colourless in an initial state and tending to discolour or to discolour(s) during storage or to discolour during the application period, and wherein said at least one coloured ingredient and said at least one colourless ingredient are selected from the group consisting of a pharmaceutically active substance and an auxiliary agent;

wherein said active substance patch comprises at least one pigment admixed into a coating on the backing layer to impart a lightness colour value $L_1$ that renders the patch optically inconspicuous on a first person's skin, in the state of having been applied to the first person's skin said patch, at a place of the skin covered with the patch, the lightness colour value $L_1$ is not less than 50% and not more than 200% of a lightness colour value $L_2$, with $L_2$ being the lightness value of the region of the skin of the same person which surrounds the applied patch, that the same applies in respect of the skin of a second or any other person, provided that $L_2$ is in the range from 5° to 100° and the pigments admixed into the coating on the backing layer range in an amount from 0.25 to 0.5 wt % and deviate from the color tone of the skin underlying the patch and the lightness colour values $L_1$ and $L_2$ are determined via a tristimulus colorimeter, wherein said patch is transparent or translucent.

2. The medical active substance patch according to claim wherein the lightness colour value $L_2$ of the first person is the tightness colour value of a person of light, Caucasian skin colour, and that the lightness colour value $L_2$ of the second person is the lightness colour value of a person of dark, Negroid skin colour, or vice versa.

3. The medical active substance patch according to claim 1, wherein said active substance patch contains at least one substance selected from the group consisting of dyes and pigments in the matrix layer or in at least one of the matrix layers.

4. The medical active substance patch according to claim 1, wherein said ingredient which is colourless in its initial state and which has a tendency to discolour or which discolour(s) during storage or during the application period is a pharmaceutical active substance.

5. The medical active substance patch according to claim 1, wherein said active substance patch is a transdermal therapeutic system.

6. A process for the production of an active substance patch according to claim 1 comprising the following steps:
a) producing a system comprising a mono- or multilayer active substance-containing matrix and a backing layer connected with said matrix, wherein the matrix is produced using a matrix polymer or matrix polymers, an active substance or active substances and auxiliary agents, and wherein at least one of said matrix and said backing layer comprises at least one substance selected from the group consisting of dyes and pigments;
b) producing at least one system according to step (a), this system being different in terms of the concentration of the dyes or/and pigments, and/or in terms of the type of the dyes or/and pigments used;
c) producing surface sections or punched pieces from the systems obtained in steps (a) and (b);
d) producing or providing colour charts having lightness colour values $L_2$, in the range from 5° to 100°;
e) applying or affixing the sections or systems obtained in step (c) to the colour charts mentioned in step (d);
f) measuring the colour values of the lightness $L_1$ of the systems located on the colour charts and determining the difference between $L_2$ and $L_1$ in each particular case; and
g) selecting those systems with a colour value of the lightness $L_1$ which is not less than 50% and not more than 200% of the lightness colour value $L_2$.

7. The medical active substance patch according to claim 1, wherein $L_2$ is in the range from 20° to 90°.

8. The medical active substance patch according to claim 1, wherein said coating is a lacquer.

9. The medical active substance patch according to claim 4, wherein said pharmaceutical active substance is nicotine.

10. The process according to claim 6, wherein step (d) comprises producing or providing colour charts having lightness colour values $L_2$ in the range from 20° to 90°.

11. The medical active substance patch according to claim 1, wherein said skin has numerical values according to the "L, a, b" system, said numerical values ranging from "5, 8, 60" to "100, 4, 0" in said "L, a, b" system.

12. The medical active substance patch according to claim 1, wherein said patch is transparent.

13. The medical active substance patch according to claim 1, wherein the backing layer is transparent.

14. The medical active substance patch according to claim 1, wherein said patch is coloured due to the presence of said pigment(s).

15. The medical active substance patch according to claim 1, wherein said patch is translucent and optically masks ingredients in which discolouration begins and intensities after the patch has been manufactured.

16. The medical active substance patch according to claim 1, wherein said coating is applied at a weight per unit area of 7 to 10 g/m².

17. The medical active substance patch according to claim 1, wherein said patch has an equally inconspicuous optical appearance when applied to a user having skin color of a Caucasian or Negroid.

* * * * *

UNITED STATES PATENT AND TRADEMARK OFFICE
CERTIFICATE OF CORRECTION

Page 1 of 1

PATENT NO. : 10,653,636 B2
APPLICATION NO. : 10/553708
DATED : May 19, 2020
INVENTOR(S) : Stefan Bracht It is certified that error appears in the above-identified patent and that said Letters Patent is hereby corrected as shown below:

In the Claims

Column 8
Claim 1, Line 55, delete "stark-skinned" and insert --dark-skinned--
Column 9
Claim 2, Line 21, insert --1-- after claim
      Line 23, delete "tightness" and insert --lightness--

Signed and Sealed this
Thirtieth Day of June, 2020

Andrei Iancu
*Director of the United States Patent and Trademark Office*